United States Patent [19]

Ahene et al.

[11] Patent Number: 5,188,844
[45] Date of Patent: Feb. 23, 1993

[54] COLOR MODIFIED MELANINS AND METHODS FOR THEIR PREPARATION AND USE

[75] Inventors: Ago B. Ahene, Newark; Miles Chedekel, Vacaville, both of Calif.

[73] Assignee: Advanced Polymer Systems, Inc., Redwood City, Calif.

[21] Appl. No.: 883,226

[22] Filed: May 7, 1992

Related U.S. Application Data

[63] Continuation of Ser. No. 523,089, May 14, 1990, abandoned.

[51] Int. Cl.$^5$ .............................................. A61K 35/36
[52] U.S. Cl. ...................................... 424/574; 424/59; 424/62; 424/63
[58] Field of Search ....................... 424/574, 59, 62, 63

[56] References Cited

U.S. PATENT DOCUMENTS

| | | | |
|---|---|---|---|
| 4,402,700 | 9/1983 | Feinland et al. | 424/70 |
| 4,698,374 | 10/1987 | Gallas | 523/100 |
| 4,806,344 | 2/1989 | Gaski | 514/939 |
| 4,806,360 | 2/1989 | Leong et al. | 424/487 |
| 4,855,144 | 8/1989 | Leong et al. | 424/487 |

OTHER PUBLICATIONS

Cosmetics Science & Technology, 2d ed, 1972, Wiley Interscience, N.Y., pp. 282-283.
Wolfram et al. (1970) J. Soc. Cosmet. Chem. 21:875-900.

*Primary Examiner*—Douglas W. Robinson
*Assistant Examiner*—Jean C. Witz
*Attorney, Agent, or Firm*—Townsend and Townsend

[57] ABSTRACT

Color modified melanin compositions are produced by exposure of a natural or synthetic melanin starting material to a color modifying agent under controlled conditions. By treating the melanin starting materials for a preselected time period, melanin products having a desired final color may be obtained. The color modified melanin may be employed in a variety of cosmetic and other topically applied formulations. Prior to incorporation in such formulations, the color modified melanins will be cleaned to remove the color modifying agent and low molecular weight degradation products of the melanin.

14 Claims, 4 Drawing Sheets

COLOR MODIFIED MELANINS AND METHODS FOR THEIR PREPARATION AND USE

This is a continuation of application Ser. No. 523,089, filed May 14, 1990, now abandoned.

BACKGROUND OF THE INVENTION

1. Field of the Invention

The present invention relates generally to melanin compositions suitable for use as ultraviolet radiation absorbents. More particularly, the present invention relates to such compositions, methods for their preparation, and methods for their use, where the melanin is color modified to enhance its suitability for incorporation into cosmetic and other topically-applied formulations.

With the growing concern over the deleterious effects of sunlight on human skin, a number of ultraviolet radiation absorbent substances have been identified and developed for use in topical sunscreen compositions. In general, the substances function by absorbing radiation in the ultraviolet radiation region and re-emitting the absorbed energy in other, less harmful radiation spectra.

Although generally effective, most of the sunscreen substances which are presently in widespread use suffer from a number of drawbacks. In particular, most of the sunscreen substances are very oily and are difficult to formulate into suitable products. Such sunscreen substances may also be incompatible with other ingredients in a cosmetic preparation where it would be desirable to incorporate sunscreen protection. Additionally, many sunscreen compositions are characterized by strong odor, usually requiring the addition of a fragrance in order to formulate a commercially-acceptable product. Furthermore, sunscreens are easily lost from the skin either by rubbing or by intradermal penetration. Finally, many of the widely used sunscreen substances can be toxic at high concentrations when absorbed through the skin.

For these reasons, it has been proposed to use melanins as the active ingredient in a wide variety of sunscreen and cosmetic formulations. Melanins are a major class of broad-spectrum ultraviolet-absorbing organic polymers found naturally in the human epidermis and elsewhere. The use of melanins as the ultraviolet-absorbent substance in sunscreen and cosmetic formulations would have a number of advantages over the prior art compositions discussed above. They are natural substances and substantially non-toxic, even when applied at very high concentrations to the skin. They are free from objectionable odor and appear to be compatible with a wide variety of formulations, including both primary sunscreen formulations and cosmetic formulations. Finally, melanins are not volatile and will not be lost from the skin through either evaporation or penetration.

In particular, it has been proposed to incorporate melanin pigments within polymeric particles in order to form melanin aggregates which may then be combined in cosmetic preparations and other formulations suitable for topical application. The incorporation of melanin pigment within the polymeric particles appears to enhance the ability of the melanins to absorb ultraviolet radiation so that such compositions afford improved protection from the sun when applied topically to the skin.

Unfortunately, most melanins are darkly colored, typically being black, dark brown, reddish brown or the like. The incorporation of such colored melanins into lightly colored cosmetic formulations can thus have an undesirable aesthetic impact. In particular, many cosmetic formulations are desired to have a pure white appearance, where the incorporation of a substantial amount of colored melanin can have a substantial deleterious effect. The incorporation of the darkly colored melanins in polymeric particles does little to improve the situation. The melanins can impart a dark hue to the polymeric particles, which in turn have an adverse effect on the color of the cosmetic formulation.

For these reasons, it would be desirable to provide color-modified melanins having a much lighter color which is compatible with the coloring of a wide variety of cosmetic formulations, particularly being compatible with white or other light colored formulations. The color modification of the melanins, however, should have little or no adverse impact on the ability of the melanins to absorb ultraviolet radiation when incorporated into the cosmetic formulations.

2. Description of the Background Art

The mechanism underlying the bleaching of melanin in hair is described in Wolfram et al. (1970) J. Soc. Cosmet. Chem. 21:875–900. The treatment of melanin pigment with oxidizing and reducing agents was generally found to induce no apparent physical change in the melanin, although treatment with hydrogen peroxide was found to cause disintegration of melanin granules. The use of solubilized melanin in cosmetic formulations is described in U.S. Pat. No. 4,806,344. The incorporation of melanins into polymeric substrates, such as plastic lenses, is described in U.S. Pat. No. 4,698,374. The incorporation of melanins into polymeric particles which in turn may be incorporated into cosmetic formulations is disclosed in U.S. Patent No. 4,806,360.

SUMMARY OF THE INVENTION

According to the present invention, a novel process for modifying the color of melanin comprises treating natural or synthetic melanin with a color-modifying agent until a preselected color has been reached. The color modification process is then stopped, and the resulting color-modified melanin may be incorporated into a wide variety of cosmetic and other formulations. Usually, the color modification will involve lightening or whitening the naturally dark color of the melanin, although conversion of the melanin to other intensely colored hues, such as orange, brown, yellow, and red, may also be possible. The method is particularly suitable for color-modifying melanins which are to be incorporated into polymeric particles. Surprisingly, the process of the present invention has been found to substantially preserve and in some cases enhance the ultraviolet absorption characteristics of the melanin, thus retaining the effectiveness of the melanin as a sunscreen component in a cosmetic or other formulation.

DESCRIPTION OF THE SPECIFIC EMBODIMENTS

Figure 1:
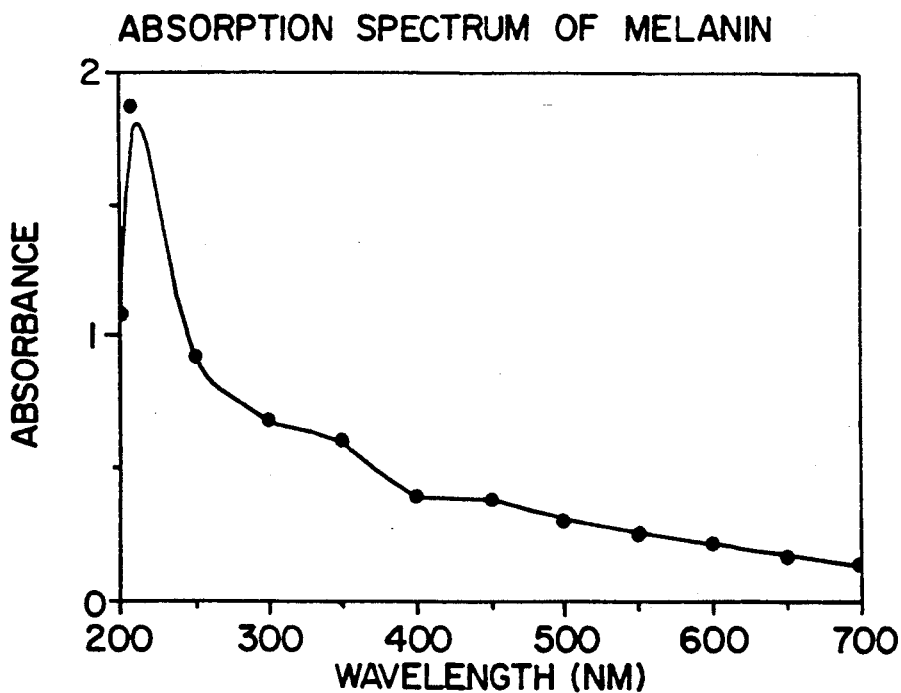
FIG. 1 is the absorption spectrum of an unmodified melanin solution having a concentration of 5 mg/100 ml.

Melanins suitable for color modification by the process of the present invention may be obtained from a wide variety of sources, including both natural and synthetic sources. For example, melanins may be isolated from a wide variety of natural sources, including human, primate, bovine, avian, rodent, cephalopod, bacterial, and fungal sources. Alternatively, melanins may be prepared synthetically by the enzymatic oxidation of numerous mono-, di-, and polyphenols, as well as by chemical and auto oxidation in a wide variety of phenolic compounds. Methods for the isolation and enzymatic synthesis of melanins are described in U.S. Pat. No. 4,806,360, the disclosure of which is incorporated herein by reference. Melanins may also be obtained by the expression of melanin genes obtained from any of the natural sources described above in cell culture. Usually, the cells grown will be recombinantly modified for over expression of the melanin gene, and the melanin recovered from the cells by conventional purification techniques.

The melanins used as the starting materials for the process of the present invention may have a wide variety of natural colors, typically being reddish orange, brown, dark brown, and black. The particular color may be quantitatively defined by any one of numerous color definition systems which have gained an acceptance over the years. A particularly useful system is designated the CIE L*a*b* System described in Principles of Color Technology. 2nd ed. (Billmeyer, F. W. and Saltzman, M. 1981) Wiley-Interscience, New York. The L* value is a measure of lightness. A perfectly white object of a clear solution has an L* value of 100. A perfect black body has an L* value of 0. The a* and b* values are chromaticity dimensions. A positive a* value is a measure of redness while a negative a* value is a measure of greenness. A positive b* value denotes yellowness and a negative b* value denotes blueness. Using this system, the color of various melanin starting materials from a variety of sources are described in Table 1 hereinbelow.

TABLE 1

| Melanin Source | Color | L* | a* | b* |
|---|---|---|---|---|
| Synthetic[1] | | | | |
| Dopa/cysteine pheomelanin[2] | yellowish brown | 79.41 | 7.38 | 26.04 |
| Dopa melanin | dark brown | 73.38 | 6.51 | 35.20 |
| Sepia melanin (solubilized) | dark brown | 76.80 | 5.49 | 33.60 |
| Hairs[3] | | | | |
| Human black hair | black | 37.34 | 0.14 | −0.29 |
| Male kangaroo | reddish brown | 53.42 | 5.37 | 9.03 |
| Female kangaroo | brown | 52.51 | 7.89 | 12.77 |
| Human fire red hair | dark brown | 42.85 | 5.91 | 7.34 |
| Red fox | light brown | 51.07 | 6.00 | 12.83 |
| Extracted Melanins | | | | |
| Sepia melanin[4] | brownish black | 36.07 | 0.53 | 0.54 |
| Recombinantly produced melanin | black | 38.08 | 0.34 | −0.58 |

[1]Based on 5 mg/100 ml melanin solution in 0.1 N NaOH.
[2]Melanins with different pheomelanin/eumelanin characteristics can be prepared by varying the ratio of dopa to cysteinyldopa or cysteine. Each mixture is incubated with mushroom tyrosinase in 0.05 M phosphate buffer, pH at 6.8, for 24 at 37° C. and then precipitated by adjusting the pH to 3 with 1M HCl. The precipitate is washed three times with pH 3 HCl, once with acetone, and then allowed to air dry.
[3]The CIE L*a*b* color space dimensions of the intact hairs and solid melanins were derived from diffuse reflectance measurements. (a) Extraction of pheomelanin from hair: Twenty grams of human red hair is soaked in 1M Na$_3$PO$_4$ overnight. The pH of the solution is lowered to 3 with 1M HCl and the precipitate collected with centrifugation at 2000 × g for 30 minutes. The crude pheomelanin is redissolved in 1 N Na$_3$PO$_4$ and reprecipitated. The cycle is repeated two more times and then dissolved in 1M NaOH and dialyzed against 0.1 N Na$_3$PO$_4$ using a bag of molecular weight cutoff of 12,000-14,000. The non-dialysable fraction is precipitated with 1 M HCl washed with acetone and dried. (b) Extraction of eumelanin from human black hair: The method of extraction of the eumelanomsomes is described by Borovansky and Hach (1972) Dermatologia, 145:37-41 and Bratosin (1973) J. Invest. Derm. 60:224-230. The melanosomes are lysed and washed to obtain the eumelanin.
[4]Crude melanin is dissected from the ink sacs of cuttle fish (Sepia officinalis) and washed with distilled water. The melanin is collected after each wash by centrifugation (2,000 g for 30 min). The melanin granules are then stirred in 8M Urea for 24 h to disassemble the melanosomes. The melanin suspension is spun down at 22,000 g for 100 min and then washed with distilled water. The pellet is washed with 50% aqueous N, N-dimethylformamide until a constant UV baseline is achieved from the washes. Finally, the pellet is washed with acetone and allowed to air dry.

The selected melanin must be solubilized or suspended in an aqueous medium prior to treatment with a color modifying agent. For most melanins, solubilization can be achieved using an alkaline solution, e.g., ammonia, while the suspension of finely dispersed melanin particles may be achieved in neutral or slightly acidic (pH below about 5) aqueous solutions. The preferred recombinant melanins may be dissolved under alkaline conditions (e.g., 0.2 M ammonia), typically at a weight ratio in the range from about 3:20 to 1:100 melanin:solution.

Once the solubilized or suspended melanin is obtained, the desired color modifying agent will be combined in the solution. The particular color modifying agent will be selected based on the nature of the melanin starting material and the desired final color. For a given melanin starting material, different colors may be obtained using different color modifying agents. Suitable color modifying agents will generally be oxidizing or reducing agents, with particular oxidizing agents including hydrogen peroxide, potassium permanganate, potassium periodate, sodium hypochlorite, and the like, and particular reducing agents being selected from sodium borohydride, sodium dithionite and the like. It is also possible to modify the color of the melanin directly without prior treatment with hydrogen peroxide. This mode of modification is exemplified by the action of potassium permanganate and sodium dithionite on melanin. Exemplary color modifying agents used with particular melanin starting materials are set forth in Table 2 hereinbelow. The table also sets forth the treatment conditions and treatment times which may be employed to achieve particular final colors.

TABLE 2

| | | Exemplary Melanin Color Modification Protocols | | |
|---|---|---|---|---|
| Melanin Source | Natural Color | Color Modifying Reagent | Treatment Conditions | Final color |
| Recombinantly Produced Melanin | black | hydrogen peroxide | 1% H$_2$O$_2$ in 0.2M NH$_4$OH for 30 minutes | grayish tan |

TABLE 2-continued

Exemplary Melanin Color Modification Protocols

| Melanin Source | Natural Color | Color Modifying Reagent | Treatment Conditions | Final color |
|---|---|---|---|---|
| (RPM) | | | | |
| RPM | black | potassium permanganate | 3% potassium permanganate | reddish yellow |
| RPM | black | hydrogen peroxide/ potassium permanganate | 1% $H_2O_2$ in 0.2M $NH_4OH$ for 30 min. then add 3% $KMnO_4$, pH 1 | yellowish tan |
| RPM | black | hydrogen peroxide/ sodium hypochlorite | 1% $H_2O_2$ in 0.2M $NH_4OH$ for 30 min., then add 5% NaOCl, pH >7 | yellowish tan |
| RPM | black | sodium hypochlorite | 5% NaOCl in 0.5M $NH_4OH$ for 20 min. | yellow |
| RPM | black | hydrogen peroxide/ peracetic acid | 1% $H_2O_2$ in 0.2M $NH_4OH$ for 30 min., then 32% peracetic acid for 10 min., pH 7-9 | light yellow tan |
| RPM | black | hydrogen peroxide/ sodium borohydride | 1% $H_2O_2$ in 0.2M $NH_4OH$ for 30 min., solid $NaBH_4$ added, stirred for 60 min. | dark grayish tan |
| RPM | black | hydrogen peroxide/ perchloric acid | 1% $H_2O_2$ in 0.2M $NH_4OH$ for 30 min. 72% $HClO_4$ for 60 min, pH <1 for 60 min. | grayish tan |
| RPM | black | hydrogen peroxide/ sodium periodate | 1% $H_2O_2$ in 0.2M $NH_4OH$ for 30 min, solid $KIO_4$ added, stirred for 16 hr. | grayish brown |
| RPM | black | hydrogen peroxide | 1% $H_2O_2$ in 0.2M $NH_4OH$ for 120 min. | light brown |
| Dopa Melanin | black | hydrogen peroxide | 1% $H_2O_2$ in 0.2M $NH_4OH$ for 60 min. | dary gray |
| Sepia Melanin | black | hydrogen peroxide | 1% $H_2O_2$ in 0.2M $NH_4OH$ for 60 min. | reddish brown |

In addition to the nature of the melanin source and the color modifying agents selected, the final color will depend on the duration of the exposure of the melanin to the color modifying agent, i.e., the treatment time. The melanins will undergo progressive color change during the treatment process, and it will be necessary to quench or otherwise stop the reaction at the time the desired color has been achieved. Usually, the necessary treatment time to achieve a particular final color will be empirically derived by exposing the melanin starting material to the particular color modifying agent under a desired set of treatment conditions. The melanin will then be periodically sampled and the color determined either visually or quantitatively. Typically, the melanins will be sampled every 10 to 20 minutes, and the color will be quantitatively measured using the CIE L*a*b* color system described above. Briefly, the sample will be diluted and the optical density measured in a spectrophotometer. The optical density readings may then be correlated with the CIE L*a*b* number. Once the desired color is achieved, the treatment time may then be employed in the subsequent preparation of melanins having the desired final color.

Quenching of the color modification reaction may be accomplished in a variety of ways depending on the particular color modification. For oxidation reactions, which are pH sensitive, quenching may be achieved by alteration of the pH. For example, in a reaction employing hydrogen peroxide, quenching may be accomplished by lowering the pH to 5 or below, typically by addition of a strong mineral acid, such as HCl. Other redox reactions may be quenched by addition of a complementary reducing or oxidizing agents such as sodium metabisulfite, sodium sulfite, ascorbic acid, and the like.

The color modified melanins must be cleaned prior to incorporation in cosmetic or other topically-applied formulations. In particular, the color modifying agents must be completely extracted and low molecular weight degradation products of the melanin should be separated. The color modifying agents may be extracted by washing or serial dilution in an aqueous solution or buffer, while the low molecular weight melanin degradation products and other proteinaceous contaminants may be removed by dialysis, molecular sieving, sizing column chromatography, or the like. Melanin degradation products having molecular weight below about 10 kD, preferably below about 20 kD, and more preferably below about 25 kD should be removed as they are potentially capable of penetrating the skin.

After cleaning, the color modified melanins may be dissolved and incorporated directly into cosmetic or other topically-applied formulations, e.g., as taught by U.S. Pat. No. 4,806,344, the disclosure of which is incorporated herein by reference. Briefly, the color-modified melanin may be combined in a variety of suitable topical vehicles, including creams, ointments, lotions, and other cosmetic and therapeutic carriers which are intended for topical application.

Alternatively, the color modified melanins may also find use in various solid polymeric substrates, as taught by U.S. Pat. No. 4,698,374, the disclosure of which is incorporated herein by reference.

Preferably, however, the melanins will be incorporated into a polymeric bead delivery system, as taught by U.S. Pat. No. 4,806,360, the disclosure of which has previously been incorporated herein by reference. The melanin may be introduced to the beads by first dissolving the melanin in an alkaline solution, followed by precipitating the melanins in the porous structure of such beads by lowering the pH. Alternatively, the melanins may be introduced to the polymeric particles by absorption of a dispersion of finely divided melanin pigment in a suitable carrier vehicle, typically having a particle size from about 0.01 to 0.1 μm. The polymeric particles may then be dried to evaporate the carrier or vehicle. The melanin will usually be present in the final polymeric bead product at from about 3 to 6 weight percent after a single absorption step. The weight concentrations of the melanin pigment may be increased to as high from about 30 to 40 weight percent by multiple absorption steps. The melanin-containing polymeric particle compositions just described are a dry powder having an aesthetically pleasing sensation when applied topically to the skin. The melanin compositions may be used alone and applied to the skin as a powder or may be incorporated in a suitable carrier base as a primary sunscreen product. Alternatively, the melanin compositions may be incorporated in other cosmetic formulations, such as skin, face, and body creams, decorative cosmetics such as foundation creams and make-up powders, lipsticks, lip balms, hair grooming preparations, and the like, where they will be generally free from interaction with other active substances in the formulations.

The following examples are offered by way of illustration, not by way of limitation.

EXPERIMENTAL

Materials and Methods

1. Characteristic spectrum of melanin:

The UV/visible spectrum of recombinantly produced melanin was obtained by dissolving 5 mg of melanin in 100 ml of 0.1 N NaOH. The UV visible absorption spectrum was recorded on a spectrophotometer between the wavelength of 200-700 nm in 1 cm path length cuvette. The spectrum is depicted in FIG. 1. There is a monotonous rise in absorbance towards the shorter wavelength. No characteristic peak or valleys are clearly visible.

2. Color modification of melanin by hydrogen peroxide:

Ten grams of melanin were dissolved or suspended in 400 ml of 0.2 M $NH_4OH$ and stirred for 1 hour. 400 ml of 2% hydrogen peroxide in 0.2 M $NH_4OH$ were added and rate of stirring increased. 100 microliter aliquots of the reaction mixture were withdrawn at various time intervals and diluted to 100 ml with 0.1M sodium hydroxide. The L*a*b* color space coordinates were calculated from the transmission curves of these solutions.

The reaction was quenched by addition of 70 mg of platinum black. Alternatively, the reaction was terminated by lowering the pH to 5 with 1M HCl and then exchanging the hydrogen peroxide in ammonium hydroxide solution with deionized water by dialysis.

The end point of the color modification process was selected from a solution whose L*a*b* color space coordinates provide appealing colors.

3. Color modification by potassium permanganate and sodium hypochlorite:

100 g dry weight of melanin was stirred in 0.2M $NH_4OH$ until the particles were finely distributed. 400 ml 0.2M $NH_4OH$ containing 2% $H_2O_2$ was added and stirred for 20 minutes. The pH was lowered to 3 with 1M HCl. The precipitate was spun down at 10,000×g for 10 minutes. 100 ml aliquots of 3% acidified potassium permanganate (pH<2) was added until there was a permanent tinge of yellow. An excess of $KMnO_4$ was added and then reduced with 100 g of sodium metabisulfite. The yellow suspension was spun down at 10,000×g for 10 minutes and then washed with 0.001 M HCl, acetone and dried in a vacuum oven at 40° C. for 16 hours at −30mm Hg. The yield in this reaction was 27.5%.

4. Color modification by sodium hypochlorite:

100 grams dry weight of melanin was suspended in 4000 ml 0.2M $NH_4OH$ and stirred for 60 minutes. 3000 ml of 5% NaOCl was added in 1000 ml increments in a total of 5 minutes. While stirring, yellow suds were observed. The solution was acidified to pH 3 and washed three times with 0.001 M HCl, then once with acetone and dried in a vacuum oven as previously described.

5. Color modification by peracetic acid:

10 grams of 30 minute sensitized melanin were stirred in 400 ml 0.2M $NH_4OH$. 30 ml of 32% peracetic acid were added in 10 ml portions keeping the pH between 7-9 with 30% ammonia solution. The reaction was allowed to proceed for 10 minutes and then 10g solid sodium sulfite was added. The reaction mixture was stirred for 30 minutes after which the pH was lowered to 2 with 1M HCl. The melanin was recovered by centrifugation and processing as described above.

6. Color modification by perchloric acid:

10 grams of melanin sensitized for 30 minutes with hydrogen peroxide were dissolved in 400 ml 0.2M $NH_4OH$. 100 ml aliquots of concentrated perchloric acid (72%) were added to a total of 500 ml. The reaction was allowed to proceed for 60 minutes. 50 g of sodium metabisulfite was added and stirred for 30 minutes. The suspension was centrifuged down and washed three times with 0.001M HCl, then once with acetone and dried in the vacuum oven (−30 mm) at 37° C. for 16 hours.

7. Color modification by sodium periodate:

10 grams of melanin were dissolved in 400 ml 0.2M $NH_4OH$. 10 g solid sodium periodate were added and stirred for 16 hours. The solution was acidified to pH 3, the ensuing precipitate was centrifuged down at 10,000×g for 10 minutes. It was then washed three times with 0.001 M HCl and once with acetone. The precipitate was dried in vacuum oven at 37° C. for 16 hours.

8. Color modification of sepia or dopa melanin by hydrogen peroxide:

Ten grams of sepia melanin were stirred in 800 ml of 1% $H_2O_2$ in 0.2M $NH_4OH$ for 60 minutes. Fifty milligrams of platinum black were added and stirred until the effervescence subsided. The undissolved pieces of melanin and the platinum black were removed by centrifugation at 10,000 g for 10 minutes. The supernatant was acidified to pH 3 with 1M HCl and washed three times with 0.001 M HCl, once with acetone, and dried in a vacuum oven at 37° C. for 16 hours.

RESULTS AND DISCUSSIONS

Figure 2:
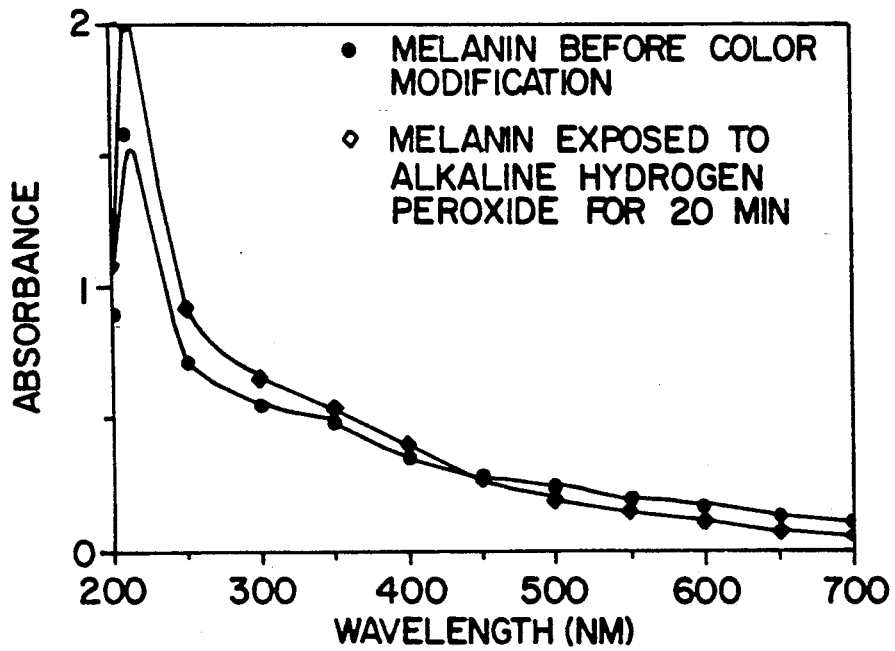
FIG. 2 compares the absorption spectra of the unmodified melanin solution of FIG. 1 with a modified melanin solution which has been exposed to 1% (by weight) $H_2O_w$ in 0.2 M $NH_4OH$ for 20 minutes.

A typical spectrum of melanin solution is shown in FIG. 1. There is a monotonous rise in the absorption spectrum towards the shorter wavelengths. No characteristic peaks or valleys are clearly discernible. The same absorption pattern is seen in color modified solutions. The absorbance of hydrogen peroxide modified solution is compared with the absorbance of recombinantly produced melanin solution in FIG. 2. There is an increase in the absorbance in the UV region when the melanin was exposed to alkaline hydrogen peroxide for 20 minutes.

Figure 3:
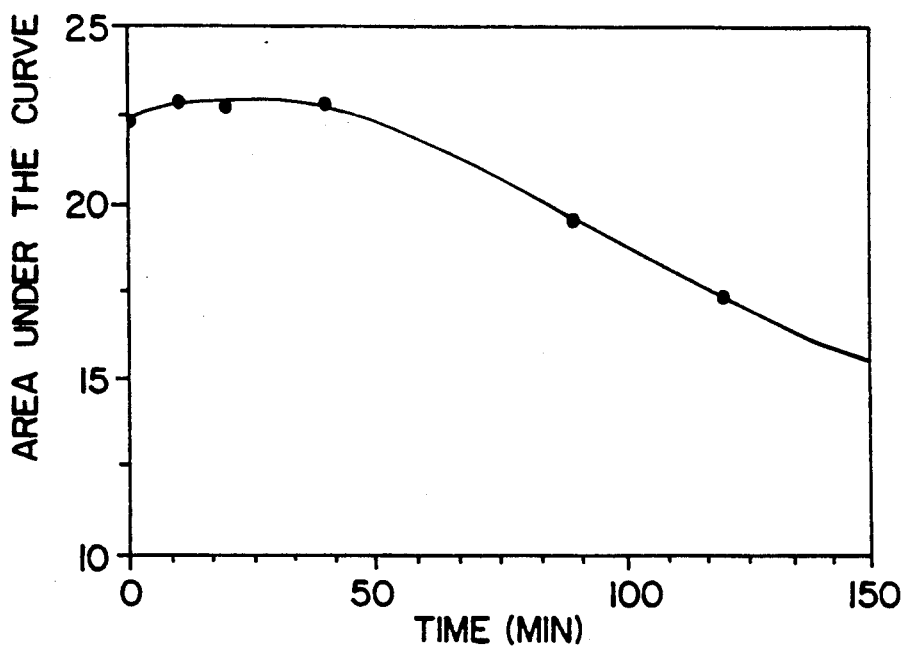
FIG. 3 illustrates the total UV absorbance displayed by melanin modified as in FIG. 2, as a function of time.

Thus, when the area under the absorption curve in UV is followed during the course of the hydrogen peroxide color modification, a curve such as FIG. 3 is observed. There is an initial increase in the area under the curve followed by a decrease. However, the maximum point does not always correspond to melanin of cosmetically appealing color, hence, the reaction may be continued until such a color is produced. The reaction medium is therefore monitored periodic determination of the CIE L*a*b* color space dimensions during the course of the reaction.

Figure 4A:
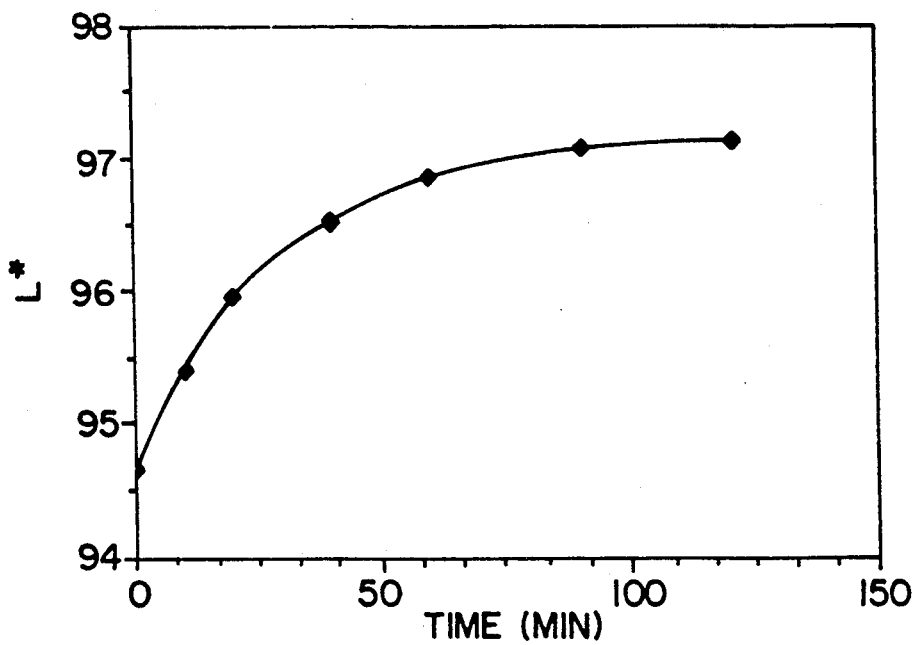
FIGS. 4(a)-4(c) illustrate the change in color coordinates of the modified melanin solution of FIG. 2 over time.
Figure 4B:
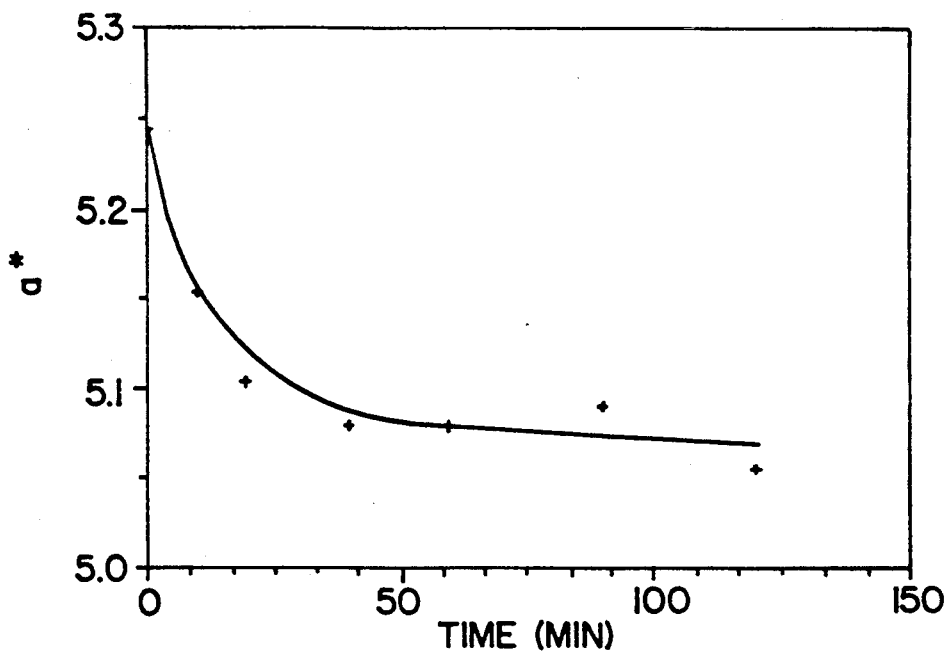
Figure 4C:
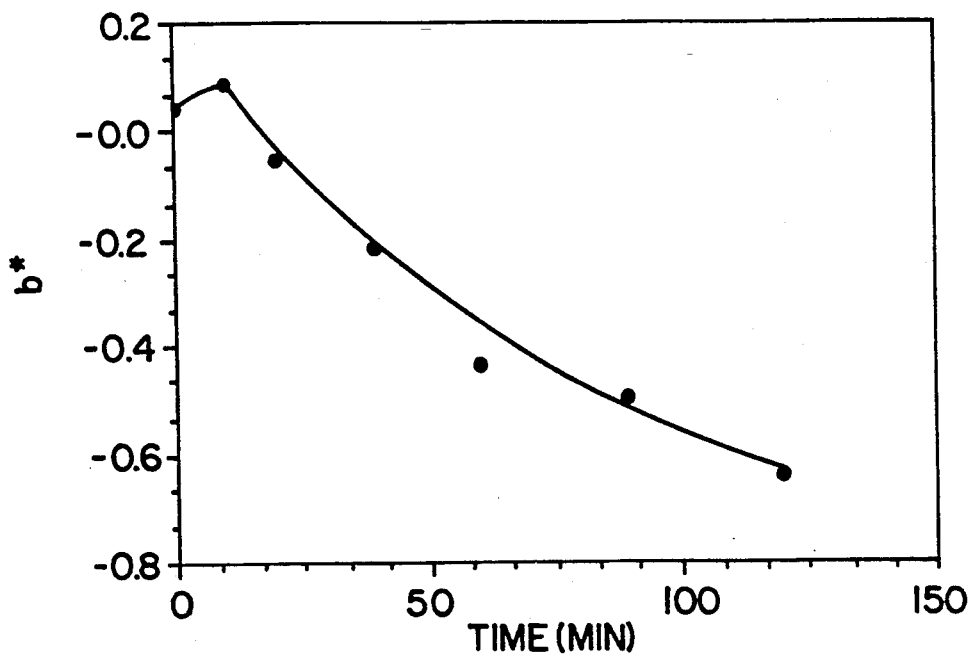

FIG. 4(a) shows the trend of L* color coordinate, which is a measure of darkness, a value of 100 is perfect white or clear solution. As the reaction progressed there was an increase in the L* until it leveled off at about 90 minutes. The other components of the CIE system are a* and b*. When a* is positive, the color is toward redness, if negative, it is greenness. The tendency toward yellowness is measured in the positive direction of b* and the negative directions measures blue. FIGS. 4(b) and 4(c) show how a* and b* change during the course of the hydrogen peroxide reaction; a* decreased rapidly and leveled off within 40 minutes of the reaction; b* on the other hand, decreased gradually until the reaction was terminated after 120 minutes. This system was applicable to the other color modification reagents described in the experimental section.

The conditions of various color modification schemes were summarized in Table 2, above. In Table 2 are colors of the formulations of the modified melanins in white cream bases.

Figure 5:
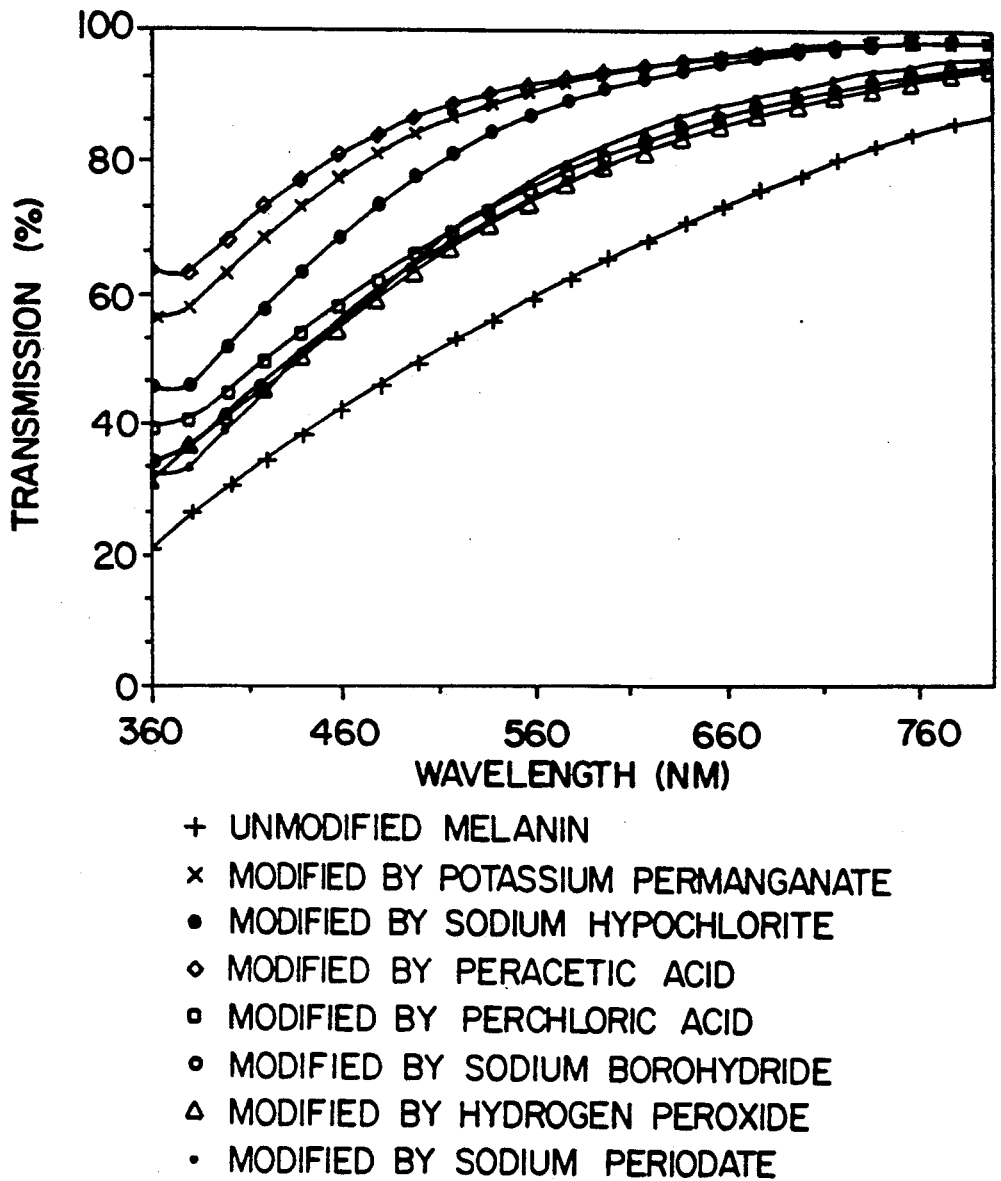
FIG. 5 is a comparison of melanin solutions modified by different modification agents.

FIG. 5 shows the transmission curves of melanin modified under different conditions. The CIE L*a*b* color space coordinates of various color modified melanins are given in Table 3. At a concentration of 5mg/100ml in 0.1N NaOH it was observed that an L* value of 88 and above generally produced melanins which when formulated with white cream base has no or diminished gray tones.

TABLE 3

Representative CIE L*a*b* Color
Space Coordinates of Color Modified Melanins

| Modifying Reagent | L* | a* | b* |
|---|---|---|---|
| Unmodified Recombinant Melanin | 80.58 | 3.81 | 18.30 |
| Potassium Permanganate | 95.54 | −0.08 | 10.48 |
| Sodium Hypochlorite | 94.65 | 0.33 | 12.79 |
| Peracetic Acid | 96.32 | −0.06 | 8.42 |
| Perchloric Acid | 88.99 | 2.04 | 15.38 |
| Sodium Borohydride | 88.06 | 2.04 | 16.46 |
| Sodium Periodate | 89.11 | 2.02 | 19.12 |
| Hydrogen Peroxide (30 minutes reaction) | 86.26 | 2.75 | 18.26 |
| Hydrogen Peroxide (120 minutes reaction) | 88.29 | 1.30 | 17.29 |

The table depicts the CIE L*a*b* color space coordinates of recombinantly produced melanin modified by various reagents as described in the text. 5 mg/100 ml of 0.1 N base solution was used to generate the data. An L* value of 88 generally produced melanins which when formulated with white cream base had diminished gray tones.

Although the foregoing invention has been described in detail for purposes of clarity of understanding, it will be obvious that certain modifications may be practiced within the scope of the appended claims.

What is claimed is:

1. A method for color modification of synthetic melanin or melanin which has bene isolated from natural sources, said method comprising:
combining a naturally dark melanin with a color modification agent selected from the group consisting of oxidizing agents and reducing agents in an aqueous medium, whereby a color modification reaction is initiated;
stopping the color modification reaction after the melanin has been lightened sufficiently so that the color is color-compatible with a human skin color; and
extracting the modification agent from the melanin.

2. A method as in claim 1, further comprising separating melanin degradation products after the color modification reaction has been stopped.

3. A method as in claim 2, wherein degradation products having a molecular weight below about 10 kD are removed.

4. A method as in claim 1, wherein the melanin is dissolved in the aqueous medium under alkaline conditions.

5. A method as in claim 1, wherein the melanin is suspended in the aqueous medium under neutral or slightly acidic conditions.

6. A method as in claim 1, wherein the oxidizing agents are selected from the group consisting of hydrogen peroxide, potassium permanganate, sodium hypochlorite, peracetic acid, and perchloric acid.

7. A method as in claim 1, wherein the initial color of the naturally dark melanin is black and the melanin is treated with hydrogen peroxide until a final color of white or tan is obtained.

8. A method as in claim 1, wherein the initial color of the melanin is black/brown and the melanin is treated with sodium hypochlorite until a final color of yellow is obtained.

9. Melanin which has been modified to have a preselected color without substantial loss of ultraviolet absorptivity produced by combining a melanin isolated from a natural source or synthetic melanin having a naturally dark color with a color modification agent selected from the group consisting of oxidizing agents and reducing agents in an aqueous medium whereby a color modification reaction is initiated;
stopping the color modification reaction after the melanin has been lightened sufficiently so that the color is color-compatible with a human skin color; and
extracting the modification agent from the melanin.

10. Melanin as in claim 9, wherein melanin degradation products having a molecular weight below about 10 kD have been separated.

11. Melanin as in claim 9, wherein the modified color is yellow, white or tan.

12. Melanin which has been modified to have a preselected color without substantial loss of ultraviolet absorptivity produced by:
combining a melanin isolated from a natural source or synthetic melanin with a color modification agent selected from the group consisting of oxidizing agents and reducing agents in an aqueous medium whereby a color modification reaction is initiated and melanin degradation products are produced;
stopping the color modification reaction after the melanin reaches the preselected color; and
separating the color modification agent and the melanin degradation products from the melanin.

13. Melanin as in claim 12, substantially free from degradation products having a molecular weight below about 10 kD.

14. Melanin as in claim 12, wherein the preselected color is yellow, white or tan.

* * * * *